United States Patent [19]

Blöcker

[11] Patent Number: 5,281,637
[45] Date of Patent: Jan. 25, 1994

US005281637A

[54] FLAMEPROOFED THERMOPLASTIC POLYESTER MOLDING MATERIAL AND ITS USE

[75] Inventor: Erich Blöcker, Hofheim am Taunus, Fed. Rep. of Germany

[73] Assignee: Hoechst AG, Frankfurt am Main

[21] Appl. No.: 4,997

[22] Filed: Jan. 15, 1993

[30] Foreign Application Priority Data

Jan. 16, 1992 [DE] Fed. Rep. of Germany ........ 4200931

[51] Int. Cl.$^5$ ............................................ C08K 5/5313
[52] U.S. Cl. ..................................... 524/100; 524/126; 544/195; 562/12; 562/14
[58] Field of Search ................ 524/100, 126; 544/195; 562/12, 14

[56] References Cited

U.S. PATENT DOCUMENTS

| | | | |
|---|---|---|---|
| 3,810,850 | 5/1974 | Rowton | 524/100 |
| 3,980,614 | 9/1976 | Noetzel et al. | 562/14 |
| 3,980,615 | 9/1976 | Noetzel et al. | 562/14 |
| 4,105,689 | 8/1978 | Auer et al. | 260/502.5 |
| 4,394,330 | 7/1983 | Hardy et al. | 260/932 |
| 4,879,327 | 11/1989 | Poisson et al. | 529/100 |
| 4,972,011 | 11/1990 | Richardson et al. | 524/131 |

FOREIGN PATENT DOCUMENTS 245207 2/1992 European Pat. Off. .
2447726 4/1976 Fed. Rep. of Germany .

OTHER PUBLICATIONS

Orbit Abstract of FR-A-2 368 495.

Primary Examiner—Veronica P. Hoke
Attorney, Agent, or Firm—Connolly & Hutz

[57] ABSTRACT

Flameproofed thermoplastic polyester molding material comprising
(A) one or more thermoplastic polyesters,
(B) a nitrogen-containing diphosphinic acid compound of the formula (I), and
(C) with or without an amine,
(D) with or without inorganic reinforcing agents, and
(E) with or without processing auxiliaries.

The nitrogen-containing diphosphinic acid compounds are effective even in relatively low concentrations and thus do not adversely affect the mechanical and electrical properties of the flameproofed polyester molding materials. The latter are used in the production of molded articles.

8 Claims, No Drawings

FLAMEPROOFED THERMOPLASTIC POLYESTER MOLDING MATERIAL AND ITS USE

The invention relates to flameproofed molding materials comprising thermoplastic polyesters that contain nitrogen-containing diphosphinic acid compounds, and their use in the production of molded articles.

Hitherto, mainly bromine-containing compounds have been used as flameproofing agents for thermoplastic polyesters, generally in combination with a synergistically acting inorganic compound (J. Troitzsch, "Kunststoffe" 80, 434–435 (1990)). On account of the ecologically questionable polybrominated diphenyl ethers and the toxic and corrosive gases produced in fires, intensive efforts are being made to develop halogen-free flameproofing agents for plastics formulations (H. Staendeke and D. J. Scharf, „Kunststoffell 79, 1200–1204 (1989)).

Phosphorus compounds are mainly used as halogen-free flameproofing systems for thermoplastic polyesters. For example, polyalkyl phosphonates are described as flameproofing agents for polyethylene terephthalate molding materials (EP-A 0,324,356). Flameproofed polybutylene terephthalate compositions are known that contain a combination of polypentaerythrityl phosphonate and melamine pyrophosphate (U.S. Pat. No. 4,278,591). For the preparation of a flame-resistant polybutylene terephthalate, the corresponding polypentaerythrityl phosphonate in combination with ammonium polyphosphate and a halogenated benzenesulfonate is also used (EP-A 0,383,978).

Flame-resistant polymer compositions containing phosphonic acid salts have also been described (EP-A 0,245,207). However, our own experiments with polybutylene terephthalate show only a slight increase in the oxygen index and thus lead to a UL 94 classification of V-2. Also, phosphinic acid salts are known as additives for producing low-flammable plastics (DE-A 2,447,726). These monofunctional, difunctional and trifunctional phosphinic acid salts contain 1, 2 or 3 nitrogen atoms in a carboxamide bond and a metal from the first three groups of the Periodic Table as cation. In the listed examples only a monophosphinic acid sodium salt is described as flameproofing agent, which additionally contains a halogen, for example bromine.

The use of flame-retardant organophosphorus additives that are readily soluble in organic solvents often has a plasticizing effect, which generally leads to a considerable deterioration in the mechanical and electrical properties of the plastic rendered flameretardant.

It is an object of the present invention to find additives that do not have the aforementioned disadvantages.

The invention relates to a flameproofed thermoplastic polyester molding material comprising (A) one or more thermoplastic polyesters
(B) a nitrogen-containing diphosphinic acid compound of the formula (I):

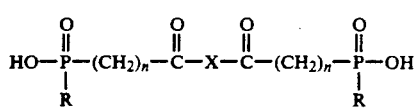

where X is the following nitrogen-containing radicals:

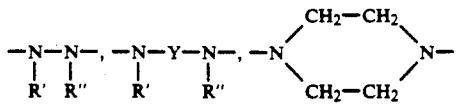

in which R is $C_1$-$C_8$-alkyl, preferably $C_1$-$C_4$-alkyl, or aryl with 6 carbon atoms, R' and R" are hydrogen or $C_1$-$C_8$-alkyl, preferably $C_1$-$C_4$-alkyl, Y is a divalent aliphatic, cycloaliphatic or aromatic hydrocarbon radical and n is the integer 1, 2, 3, 4 or 5, preferably 1 or 2, 2 being particularly preferred, and (C) with or without an amine,
(D) with or without inorganic reinforcing agents, and
(E) with or without processing auxiliaries.

The invention also provides flameproofed thermoplastic polyester molding materials in which the component (C) has been reacted with the component (B) to form a salt (component (BC)), and the component (BC) is used instead of the two individual components.

The nitrogen-containing, halogen-free diphosphinic acids can, on account of their symmetrical structure and their high melting point of in general more than 200° C., be incorporated in thermoplastic polyesters such as polybutylene terephthalate and polyethylene terephthalate without substantially damaging the latter, and above a certain concentration act as flameproofing agents. The required amount of the flameproofing agent depends on the polyester and any reinforcing agent or filler that may have been used. Also, these diphosphinic acids generally do not produce any undesirable plasticizing of the polyesters.

The polyesters (A) that are used according to the invention are polycondensation products of aromatic dicarboxylic acids and aliphatic diols or their respective reactive derivatives. Up to 10 mol % of the aromatic dicarboxylic acid may be replaced by another dicarboxylic acid. Similarly, up to 10 mol % of the aliphatic diol, which for example may also be 1,4-dimethylolcyclohexane, may be replaced by another diol, including for example by a polyether diol so that the properties of the polyester employed may be varied. Polybutylene terephthalate is preferred as polyester in the flameproofed polyester molding materials on account of its rapid crystallization from the melt. However, polyethylene terephthalate is also used for polyester molding materials, preferably if it contains nucleation agents and, if desired, also organic plasticizers as crystallization accelerators, so that it crystallizes sufficiently rapidly during the processing into molding materials. Mixtures of various polyesters may also be used, for example mixtures of PBT and PET. The individual polyesters are compounded together with the flameproofing components and the further additives, and processed.

The diphosphinic acids (B) that are used are obtained by a chemical reaction of for example a 2,5-dioxo-1,2-oxaphospholane substituted by alkyl or aryl in the 2-position (hereinafter termed oxaphospholane) with diamines:

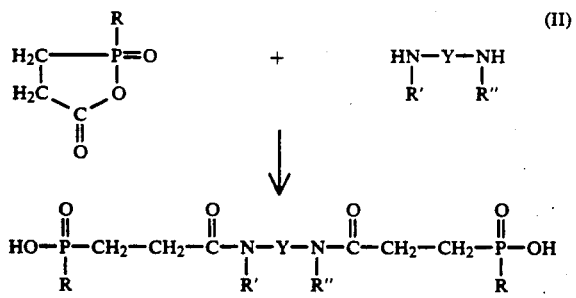

where Y, R, R' and R" are as defined above.

Piperazine may for example also be used as dismine:

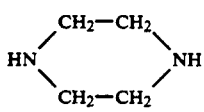

The reaction of the oxaphospholane with the dismine is preferably carried out in the presence of a liquid reaction medium in which the starting substances are soluble at room temperature or elevated temperature, preferably at 80° to 150° C. Depending on the reactivity of the dismine used, the reaction is performed by heating the mixture of the reactants in the solvent (in the case of aromatic diamines) or by metered addition of one of the two reactants at elevated temperature, preferably from at least 80° C., to the solution of the other starting component (in the case of aliphatic diamines), since in this case an exothermic reaction takes place. The reaction product generally precipitates out from the solvent in the form of a crystalline, sparingly soluble compound at the reaction temperature or at lower temperatures, and can be isolated from the solvent by conventional methods. The compounds listed in Table 1 were obtained by reacting 2-methyl-2,5-dioxo-1,2-oxaphospholane with various diamines in dimethylformamide as reaction medium.

The diphosphinic acid flame retardants (B) may be added as such to the polyesters (A). On account of their symmetrical structure and their resultant high melting point, they do not in general lead to a substantial interaction with the polyester matrix, i.e. do not produce any significant decomposition of the polyester or any consequential serious deterioration in the physical properties of molded articles produced from the polyesters. The amount of diphosphinic acids to be added to the polyesters as flame retardant may vary within wide limits. In general 1 to 40 parts by weight are used, based on 100% of the total mixture, preferably 5 to 30 parts by weight, and in particular 10 to 25 parts by weight. The optimum amount depends on the polyester or polyester mixture that is used and on the diphosphinic acid component that is employed, and can easily be determined experimentally. Since the diphosphinic acids are generally effective even in small amounts, they produce fewer undesirable effects in the polyester compared to other known phosphorus-based flameproofing agents.

It is also possible to add suitable thermally stable, not readily volatile amines as a further additive in the preparation of the flameproofed polyester mixture. These amines can then react at least in part, depending on the amount added, in the polyester melt during the compounding process and during the injection molding with the added diphosphinic acid, with the formation of a salt but without elimination of water. In this way a partial or complete neutralisation of the phosphinic acid groups of the flame retardant may be effected, whereby, depending on the circumstances, the interaction of the diphosphinic acid (B) with the polyester matrix (A) is reduced further or is even completely prevented, and the physical properties of the flameproofed polyester mixture or the molded articles produced therefrom are improved. Accordingly, during the compounding the properties of the flameproofed mixture can be specifically adjusted and optimized by the separate addition of the phosphinic acid and amine components.

Amines that are particularly suitable for incorporation into the flameproofed polyester molding materials according to the invention are 1,3,5-triazine derivatives, for example 2,4,6-triamino-1,3,5-triazine (melamine) or 2,4-diamino-6-phenyl-1,3,5-triazine (benzoguanamine). Other amino compounds may however also be used as long as they are not substantially volatile at the compounding temperatures.

It is also possible first of all to prepare amine salts from the diphosphinic acids and use these as flameproofing additive (BC). For example, the corresponding amine salts can be prepared from the diphosphinic acids (B) and the amines (C), for example melamine, by reaction in a polar solvent, preferably in the aqueous phase and at elevated temperatures, in the molar ratio 1:1 or 1:2. These salts used as flameproofing agents in polyesters lead to practically the same product properties as an addition of the individual components.

As inorganic reinforcing agents (D) there may be used glass fibers, glass spheres and mineral fillers, or mixtures thereof.

Furthermore, the compositions according to the invention may contain further conventional additives and processing auxiliaries (E) such as mold release agents, flow auxiliaries, crystallization auxiliaries, heat and light stabilizers, uv absorbers, antioxidants, antistats, coupling agents, anti-drip agents, colorants and color pigments, and also further flameproofing additives and agents for reducing smoke formation. These substances may in each case be used individually or in combination with one another.

The mixtures of the thermoplastic polyesters, the nitrogen-containing diphosphinic acid compound, and, if desired, the further additives may be prepared in known mixing apparatus such as rollers, kneaders, single-screw and multi-screw extruders. Double-screw extruders are preferred in order to achieve as homogeneous a distribution as possible of all the components in the polyester molding materials.

The thus prepared flameproofed materials can be processed into molded articles in conventional processing apparatus, for example using injection molding machines. Films and fibers can also be produced.

EXAMPLES

I. Preparation of the diphosphinic acids

I.1. Diphosphinic acid II (see Table 1) (Use of an aromatic dismine) 173 g of 1,3-phenylene dismine, 453 g of 2-methyl-2,5-dioxo-1,2-oxaphospholane and 4.0 l of dimethylformamide were added to a 10 l capacity flask and heated and dissolved while stirring. The reaction product began to precipitate out when the internal temperature reached about 100° C., a thick crystal paste being formed within a few minutes. The reaction temperature was then kept at 105°±5° C. for about 2 hours.

An increase in the reaction temperature to above 120° C. is not critical, the only disadvantage being that the yield of reaction product is smaller. After cooling to room temperature the product that had crystallized out was suction filtered and washed with methanol until the filtrate was colorless. Yield after drying about 565 g (about 94% of theory); for properties see Table 1.

I.2 Diphosphinic acid VI (see Table 1) (Use of an aliphatic dismine)

670 g of 2-methyl-2,5-dioxo-1,2-oxaphospholane and 5.0 l of dimethylformamide were heated to about 95°±5° C. in a 10 l capacity flask equipped with a stirrer, and 144 g of 1,2-diaminoethane were added dropwise, whereupon the temperature of the reaction mixture rose without any additional heating on account of the exothermic reaction. The addition of the dismine was metered so that the internal temperature did not rise above 140° C., preferably not above 130° C. During the addition of the dismine the diphosphinic acid precipitated out from the reaction mixture. After the end of the addition the reaction mixture was then stirred for another 2 hours at 120°±10° C. and, after cooling to room temperature, the product was suction filtered and washed with methanol. Yield after drying, about 750 g (about 95% of theory), for properties see Table 1.

The further diphosphinic acids listed in Table I were prepared in a similar way.

II. Preparation, processing and testing of the molding materials

The polyesters were used either in the form of granules or as comminuted material. The starting polyester, for example polybutylene terephthalate or nucleated polyethylene terephthalate, was mixed with the organic additives (flameproofing agents and if desired further additives) and melted and mixed in a double-screw extruder, for example a ZSK 25 extruder from Werner & Pfleiderer (Stuttgart, Federal Republic of Germany) and extruded into strands and granulated. The melt temperatures depend on the polyester mixture used, but are generally from 240° to 280° C. In the preparation of glass fiber-reinforced or mineral-filled polyester compositions, the glass fiber or mineral is metered separately from the starting mixture via a second hopper of the double-screw extruder into the already molten mass.

After adequate drying, for example 2 to 6 hours at 120° C., the molding materials were injection molded to give molded articles, specifically standard test bar, in the conventionally employed injection molding machines at similar melt temperatures as in extrusion and at a mold temperature of from 80° to 130° C. The ultimate tensile strength and the elongation at break were measured on the bars according to DIN 53455, and the IZOD notched impact strength was measured according to ISO Standard 180/1A.

The flammability was tested in accordance with the guidelines laid down by Underwriters Laboratories Inc. (UL 94 test).

The amounts of the components used are given in % by weight in the following examples.

EXAMPLES 1 TO 8 AND COMPARATIVE EXAMPLE 1 (TABLE 2)

Polyester molding materials according to the invention were prepared in a non-reinforced form by extruding polybutylene terephthalate (PBT) with various diphosphinic acids (see Table 1) in different concentrations and in some cases with added melamine. The formulations, results of the burning tests and some mechanical properties of injection-molded standard test pieces are summarized in Table 2. PBT without the additives was used as Comparative Example 1.

EXAMPLES 9 TO 19 AND COMPARATIVE EXAMPLE 2 (TABLE 3)

Glass fiber-reinforced polyester molding materials were prepared by extruding PBT with various diphosphinic acids (see Table 1), in some cases with the addition of amine base and glass fibers. The formulations and test results are summarized in Table 3 in a similar manner to Examples 1-8 (Table 2), together with a Comparative Example 2 that did not contain diphosphinic acid or amine.

EXAMPLES 20, 21 AND COMPARATIVE EXAMPLE 3 (TABLE 4).

Glass fiber-reinforced polyester molding materials of polyethylene terephthalate (PET) were prepared by extruding ®Impet 2600 GV 1/30 (rapidly crystallizing PET with 30% of glass fiber reinforcement, melt volume index NVI [265° C./2.16 kg] 8 cm$^3$/10 minutes, produced by Hoechst AG, Frankfurt am Main, Federal Republic of Germany) with various diphosphinic acids (see Table 1), with and without added amine base. In the Comparative Example 3 melamine cyanurate was incorporated as additive instead of the diphosphinic acid and amine into the PET. The formulations and test results are summarized in Table 4.

EXAMPLES 22 AND 23 (TABLE 5)

Two different melamine salts were prepared from the diphosphinic acid II (DPA II) from Table 1:

a) DPA II melamine salt 1:1

By dissolving molar amounts of DPA II and melamine in water at 90°-100° C. and crystallization on cooling.
Analysis:
P content calculated 12.35%, found 12.1/12.4%
N content calculated 22.3%, found 22.2/22.4% b) DPA II melamine salt 1:2

By dissolving the DPA II with twice the molar amount of melamine in water at 90°-100° C. and crystallization on cooling.
Analysis:
P content calculated 9.9%, found 9.7/9.8% N content calculated 31.2%, found 31.0/31.2%

These diphosphinic acid meldmine salts were incorporated in glass fiber-reinforced polyester molding materials in an extruder by mixing with polybutylene terephthalate and glass fibers. The formulations and test results are given in Table 5.

TABLE 1

Diphosphinic acids

| Comp. Ex. | X | M g/ml | Color | Melting point (DSC °C. peak) | % P Calc. % | % P Found % | % N Calc. % | % N Found % | Yield %[2] | DMF per mole of product |
|---|---|---|---|---|---|---|---|---|---|---|
| I | —HN—⌬—CH₂—⌬—NH— | 466 | white | 286 | 13.3 | 13.0/13.2 | 6.0 | 5.9/5.9 | 93 | 4.0 |
| II | —HN—⌬—NH— (meta) | 376 | white | 252 | 16.5 | 15.9/16.0 | 7.4 | 7.3/7.4 | 94 | 2.5 |
| III | —HN—⌬—NH— (para) | 376 | white | 310–320 | 16.5 | 16.0/16.2 | 7.4 | 7.4/7.4 | 96 | 3.8 |
| IV | —N⟨piperazine⟩N— | 354 | slightly yellowish | 244 | 17.5 | 17.2/17.5 | 7.9 | 8.0/8.0 | 98 | 0.9 |
| V | —HN—NH—[1] | 300 | white | 243 | 20.7 | 20.5/20.6 | 9.3 | 9.3/9.3 | 45[3] | 1.4 |
| VI | —HN—(CH₂)₂—NH— | 328 | white | 240 | 18.9 | 18.6/18.9 | 8.5 | 8.5/8.5 | 95 | 1.9 |
| VI | —HN—(CH₂)₆—NH— | 384 | white | 219 | 16.1 | 15.8/16.0 | 7.3 | 7.4/7.4 | 68[3] | 2.0 |

[1] Used: hydrazine hydrochloride
[2] Calculated as diamine, with 5 mol % excess of oxaphospholane
[3] Yields not optimized.

TABLE 2

| | Example 1 | 2 | 3 | 4 | 5 | 6 | 7 | 8 | Comparative Example 1 |
|---|---|---|---|---|---|---|---|---|---|
| PBT | 81.1 | 82.0 | 87.0 | 86.0 | 83.7 | 82.4 | 84.8 | 83.4 | 100 |
| Diphosphinic acid II | 12.0 | 15.0 | — | — | — | — | — | — | — |
| Diphosphinic acid IV | — | — | 13.0 | 14.0 | 12.0 | 13.0 | — | — | — |
| Diphosphinic acid VI | — | — | — | — | — | — | 11.0 | 12.0 | — |
| Melamine | 6.2 | 3.0 | — | — | 4.3 | 4.6 | 4.2 | 4.6 | — |
| P content, calc. (%) | 2.0 | 2.5 | 2.3 | 2.5 | 2.1 | 2.3 | 2.1 | 2.3 | — |
| N content, calc. (%) | 5.0 | 3.1 | 1.0 | 1.1 | 3.8 | 4.1 | 3.7 | 4.1 | — |
| Fire class UL 94, 1.6 mm | V-2 | V-0 | V-2 | V-2 | V-0 | V-0 | V-0 | V-0 | — |
| Total flaming combustion time (sec) | 2 | 2 | 2 | 2 | 2 | 2 | 2 | 2 | — |
| Ultimate tensile strength (N/mm²) | 43 | 55 | 60 | 61 | 49 | 48 | 59 | 55 | 58 |
| Elongation at break (%) | 1.4 | 2.1 | 3.3 | 3.4 | 1.8 | 1.7 | 2.6 | 2.3 | 3.6 |
| Izod notched impact strength at 23° C. (mJ/mm²) | 1.9 | 1.9 | 3.0 | 3.0 | 1.1 | 1.8 | 2.3 | 2.1 | 3.5 |

TABLE 3

| | Example 9 | 10 | 11 | 12 | 13 | 14 | 15 | 16 | 17 | 18 | 19 | Comparative Example 2 |
|---|---|---|---|---|---|---|---|---|---|---|---|---|
| PBT | 52.0 | 55.0 | 53.3 | 52.5 | 50.0 | 55.0 | 52.0 | 50.0 | 52.9 | 48.4 | 51.4 | 70 |
| Diphosphinic acid I | 15.0 | — | — | — | — | — | — | — | — | — | — | — |
| Diphosphinic acid II | — | 15.0 | 12.0 | 15.0 | 15.0 | — | — | — | — | — | — | — |
| Diphosphinic acid III | — | — | — | — | — | 15.0 | 13.5 | 15.0 | — | — | — | — |
| Diphosphinic acid IV | — | — | — | — | — | — | — | — | 12.6 | 12.6 | 13.7 | — |
| Melamine | — | — | 4.7 | 2.5 | 5.0 | — | 4.5 | 5.0 | 4.5 | 9.0 | 4.9 | — |
| Benzoguanamine | 3.0 | — | — | — | — | — | — | — | — | — | — | — |
| Glass fibers | 30 | 30 | 30 | 30 | 30 | 30 | 30 | 30 | 30 | 30 | 30 | 30 |
| P content, calc. (%) | 2.0 | 2.5 | 2.0 | 2.5 | 2.5 | 2.5 | 2.2 | 2.5 | 2.2 | 2.2 | 2.4 | |
| N content, calc. (%) | 2.0 | 1.1 | 4.0 | 2.8 | 4.4 | 1.1 | 4.0 | 4.4 | 4.0 | 7.0 | 4.3 | |
| Fire class UL 94, 1.6 mm | V-2 | V-0 | V-0 | V-0 | V-0 | V-0 | V-0 | V-0 | V-0 | V-0 | V-0 | — |
| Total flaming combustion time (sec) | 8.3 | 7.9 | 6.4 | 3.9 | 3.0 | 5.0 | 5.0 | 4.0 | 9.8 | 3.0 | 6.0 | — |
| Ultimate tensile strength (N/mm²) | 119 | 133 | 160 | 141 | 144 | 130 | 143 | 135 | 136 | 126 | 142 | 155 |
| Elongation at break (%) | 1.2 | 1.6 | 2.2 | 1.9 | 2.1 | 2.3 | 2.1 | 1.9 | 2.1 | 1.7 | 2.1 | 2.8 |
| Izod notched impact strength | 5.2 | 5.1 | 7.5 | 6.8 | 8.7 | 5.9 | 5.8 | 6.1 | 8.4 | 7.9 | 7.7 | 9.7 |

TABLE 3-continued

|  | Example |  |  |  |  |  |  |  |  |  |  | Comparative Example 2 |
|---|---|---|---|---|---|---|---|---|---|---|---|---|
|  | 9 | 10 | 11 | 12 | 13 | 14 | 15 | 16 | 17 | 18 | 19 |  |
| at 23° C. (mJ/mm²) |  |  |  |  |  |  |  |  |  |  |  |  |

TABLE 4

|  | Example | | Comparative Example 3 |
|---|---|---|---|
|  | 20 | 21 | |
| ® Impet 2600 GV 1/30[1] | 88.0 | 85.4 | 85.0 |
| Diphosphinic acid III | 12.0 | — | — |
| Diphosphinic acid VI | — | 10.5 | — |
| Melamine | — | 4.1 | — |
| Melamine cyanurate | — | — | 15.0 |
| P content, calc. (%) | 2.0 | 2.0 | — |
| N content calc. (%) | 0.9 | 3.6 | 7.4 |
| Fire class UL 94, 1.6 mm | V-0 | V-2 | failed |
| Total flaming combustion time (sec) | 5 | 4 | |
| Ultimate tensile strength (N/mm²) | 90 | 43 | 84 |
| Elongation at break (%) | 1.3 | 0.7 | 1.1 |
| Izod notched impact strength at 23° C. (mJ/mm²) | 4.5 | | |

[1] PET from Hoechst AG, containing 30% by weight of glass fibers

TABLE 5

|  | Example | |
|---|---|---|
|  | 22 | 23 |
| PBT | 50 | 50 |
| DPA II/Melamine salt 1:1 | 20 | — |
| DPA II/Melamine salt 1:2 | — | 20 |
| Glass fibers | 30 | 30 |
| P content, calc. (%) | 2.5 | 2.0 |
| N content calc. (%) | 4.4 | 6.2 |
| Fire class UL 94, 1.6 mm | V-0 | V-1 |
| Total flaming combustion time (sec) | 2.6 | 16.0 |
| Ultimate tensile strength (N/mm²) | 142 | 104 |
| Elongation at break (%) | 2.1 | 1.3 |
| Izod notched impact strength at 23° C. (mJ/mm²) | 7.8 | 6.3 |

I claim:

1. Flameproofed polybutylene terephthalate polyester molding material comprising
   (A) polybutylene terephthalate, and
   (B) a nitrogen-containing diphosphinic acid compound of the formula (I):

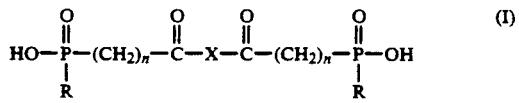

where X is one of the following nitrogen-containing radicals:

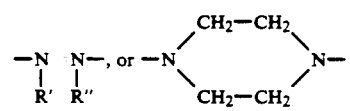

R is $C_1$-$C_8$-alkyl or aryl with 6 carbon atoms, R' and R" are hydrogen or $C_1$-$C_3$-alkyl, and n is the integer 1, 2, 3, 4 or 5.

2. A molded article produced from the flameproofed polyester molding material of claim 1.

3. A molding material as claimed in claim 1, further comprising at least one inorganic reinforcing agent.

4. A molding material as claimed in claim 1, further comprising at least one processing auxiliary.

5. A molding material as claimed in claim 1, further comprising at least one inorganic reinforcing agent and at least one processing auxiliary.

6. A molding material as claimed in claim 3, wherein said inorganic reinforcing agent is selected from the group consisting of glass fibers, glass spheres and mineral fillers.

7. A molding material as claimed in claim 4, wherein said processing auxiliary is selected from the group consisting of crystallization auxiliaries, mold release agents, anti-drip agents, stabilizers, flow auxiliaries, colorants and plasticizers.

8. A molding material as claimed in claim 7, wherein the anti-drip agent comprises 0.01-5 parts by weight of fluorinated polyolefins.

* * * * *

UNITED STATES PATENT AND TRADEMARK OFFICE
CERTIFICATE OF CORRECTION

PATENT NO. : 5,281,637
DATED : January 25, 1994
INVENTOR(S) : Erich Blocker

It is certified that error appears in the above-indentified patent and that said Letters Patent is hereby corrected as shown below:

In claim 1, at column 10, line 23, "$C_1$-$C_3$-alkyl" should read --$C_1$-$C_8$-alkyl--.

Signed and Sealed this

Twentieth Day of September, 1994

Attest:

BRUCE LEHMAN

*Attesting Officer*   *Commissioner of Patents and Trademarks*